United States Patent [19]

Woell

[11] Patent Number: 5,093,538
[45] Date of Patent: Mar. 3, 1992

[54] PROCESSES FOR THE CONVERSION OF MYRCENE TO CITRAL

[75] Inventor: James B. Woell, Lawrenceville, N.J.

[73] Assignee: Union Camp Corporation, Wayne, N.J.

[21] Appl. No.: 471,180

[22] Filed: Jan. 26, 1990

Related U.S. Application Data

[63] Continuation-in-part of Ser. No. 363,808, Jun. 9, 1989, Pat. No. 4,978,804, and Ser. No. 269,278, Nov. 9, 1988, Pat. No. 5,017,726.

[51] Int. Cl.$^5$ .................... C07C 45/00; C07C 45/43
[52] U.S. Cl. ................... 568/491; 568/448; 568/449; 568/485
[58] Field of Search ............. 568/448, 485, 491, 449

[56] References Cited

FOREIGN PATENT DOCUMENTS 7605749 12/1976 Netherlands ................. 568/485

OTHER PUBLICATIONS

Fahey et al., "Journal of Organic Chemistry", vol. 39, pp. 3276-3277 (1974).

Primary Examiner—Werren B. Lone
Attorney, Agent, or Firm—William K. Wissing

[57] ABSTRACT

A novel process for converting myrcene to citral using palladium (II) chloride in the presence of water, an immiscible solvent, a phase transfer agent, and a metal oxoanionic salt. A novel process for converting a palladium-myrcene complex to citral using a phase transfer agent and a metal oxoanionic salt in the presence of water and an immiscible solvent is also disclosed.

25 Claims, No Drawings

PROCESSES FOR THE CONVERSION OF MYRCENE TO CITRAL

RELATED APPLICATION

This application is a continuation-in-part of copending applications U.S. Ser. No. 363,808 filed June 9, 1989, now U.S. Pat. No. 4,978,804, issued Dec. 18, 1990, and U.S. Ser. No. 269,278 filed Nov. 9, 1988, now U.S. Pat. No. 5,017,726.

BACKGROUND OF THE INVENTION

The availability of adequate supplies of monoterpene aldehydes, particularly citral, is an issue of great importance to a number of industries. Although some processes for the commercial production of citral are available, new and/or improved synthetic routes are needed.

Organometallic chemistry has been used by a number of researchers in an attempt to effect various monoterpene transformations. Early experiments are reported in McQuillin et.al., *J. Chem. Soc. Perkin Trans.* pp. 809-815 (1974), and Dunne et.al., J. Chem. Soc. (C), pp. 2196-2200, 2200-2203, and 2203-2206 (1970). In these studies, the authors prepared several allyl palladium complexes of terpene compounds, including those resulting from the reaction of palladium with myrcene. Cyclization of myrcene, however, was found to occur, and citral was never obtained from the described processes.

Adding to this earlier work, Takahashi et.al., *Journal of Organometallic Chemistry*, Vol. 266, pp. 327-336 (1984) successfully prepared a mixture of citral and nerol utilizing a two-step method. First, myrcene was reacted with dichlorobis(acetonitrile)palladium in the solvent hexamethylphosphoric triamide (HMPA) or in the presence of a base such as $Li_2O_3$ using dimethylformamide (DMF) as solvent, to yield a non-cyclized palladium-myrcene complex. Although the reported yield for the HMPA process was relatively good, the $Li_2CO_3$/DMF process yield was somewhat low, approximately 33%. In the second step of the reported process, the complex was isolated, and then treated with base to yield terpene aldehydes and alcohols such as citral and nerol. One major drawback of these processes, however, is that they necessitate two steps, requiring isolation of the intermediate before further processing. Moreover, the product obtained using these methods is a mixture of both citral and nerol. Furthermore, the reactions are saddled with the added disadvantage of a temperature limitation, since at temperatures above about 60° C. the solvents HMPA and DMF are decomposed by the palladium species. See Bombieri et. al., *Inorganic Chimica Acta*, Vol. 86, pp. 121-125 (1984); Fahey et.al., *Journal of Organic Chemistry*, Vol. 9, pp. 3276-77 (1974). In addition, the use of HMPA in this, or any process, is clearly undesirable, since HMPA is an extremely potent toxin, as well as a suspected carcinogen.

Citral is a compound of high significance to the flavor, fragrance and synthetic vitamin industries. Additional and/or better processes for their commercial production, particularly processes employing the readily available starting material myrcene, are needed. The present invention is directed to this very important end.

SUMMARY OF THE INVENTION

The present invention provides a novel and highly efficient process for the production of citral comprising contacting myrcene with palladium (II) chloride in the presence of water, an immiscible solvent, a phase transfer agent, and a metal oxoanionic salt. The phase transfer agent is preferably an onium salt such as an ammonium, phosphonium or sulfonium salt. Preferably, the process is carried out in the presence of an oxidizing agent. Also, preferably, the process is conducted at temperatures ranging from about 80° C. to about 90° C.

The present invention also provides a process for producing citral comprising contacting a palladium-myrcene complex of the formula

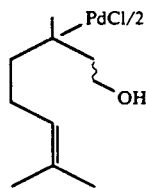

with a phase transfer agent, and a metal oxoanionic salt, in the presence of water and an immiscible solvent. Preferably, the phase transfer agent is an onium salt such as an ammonium, phosphonium or sulfonium salt. Also preferably, the process is carried out at temperatures ranging from about 80° C. to about 90° C.

Using the foregoing processes, citral production can be efficiently and effectively carried out with a high yield of and high selectivity to this very important end product.

DETAILED DESCRIPTION OF THE INVENTION

The subject invention involves the production of the monoterpene aldehyde citral (that is, 3,7-dimethyl-(E,Z)-2,6-octadienal), a compound of significant importance to the flavor, fragrance and synthetic vitamin industries. Specifically, in one aspect, the present invention provides a two-phase system for the direct production of citral comprising contacting myrcene with a palladium (II) chloride in the presence of water, an immiscible solvent, a phase transfer agent, and a metal oxoanionic salt.

The myrcene employed in the subject processes may be pure myrcene or other suitable mixtures of compounds containing myrcene, as will be apparent to those skilled in the art. One readily available and relatively inexpensive source of myrcene is a myrcene and limonene mixture in a ratio of about 80 to about 20, respectively, a product which is commercially available from Aldrich Chemical Company, Milwaukee, Wisconsin. Since myrcene is relatively unstable to oxygen, it is preferable to utilize a myrcene mixture containing an antioxidant such as 2,6-di-tertiary-butyl-4-methylphenol, commonly referred to as butylated hydroxy toluene (BHT) and sold under the trademark Ionol by Shell Chemical Company, New York, N.Y.

The palladium (II) chloride may be added directly as $PdCl_2$. Alternatively, it may be formed in situ by the addition of a source of chloride ion, such as LiCl or NaCl, to a palladium (II) salt, such as $PdSO_4$, $Pd(NO_3)_2$, $Pd_3(PO_4)_2$ and $Pd(BF_4)_2$. Other sources of chloride ion and palladium (II) salts suitable for in situ generation of the palladium (II) chloride will be apparent to those skilled in the art. If desired, the PdCl$_2$ compound may be complexed with loosely coordinated ligand donors, such as acetonitrile, benzonitrile, 1,5-cyclooctadiene and dimethyl sulfoxide. Thus, the palladium (II) chloride may be in the form of, for example, dichlorobisaceto-nitrile palladium, that is, PdCl$_2$(CH$_3$CN)$_2$. Other suitable ligand donors for coordination with the PdCl$_2$ compound will be apparent to those skilled in the art. These and other obvious variations are intended to be within the ambit of the phrase palladium (II) chloride, as used herein. Preferably, the palladium (II) chloride is PdCl$_2$ or PdCl$_2$(CH$_3$CN)$_2$.

As used herein, the term immiscible, employed in connection with the term solvent, denotes those liquids which will not substantially mix with water, thus enabling the formation of a two-phase system under the conditions of the subject process. Suitable immiscible solvents will be readily apparent to those skilled in the art and include substituted and unsubstituted aromatic compounds, as well as substituted C$_3$ to C$_{12}$ alkyls wherein the alkyl is substituted with one or more of such functionalities as hydroxy, ketone, ether or cyano groups. Examples of suitable aromatics include benzene, toluene, and xylene. Examples of suitable substituted alkyls include butanol, pentanol and hexanol. Other suitable immiscible solvents will be apparent to those skilled in the art. Preferably, the solvent is a substituted aromatic compound or a substituted C$_3$ to C$_{12}$ alkyl wherein the alkyl is substituted with one or more hydroxy groups. More preferably, the solvent is selected from the group consisting of toluene and butanol. Not only do the preferred immiscible solvents of the invention provide, in combination with the water employed in the present process, a two-phase system which efficiently and effectively promotes the conversion of myrcene to citral, in addition, these solvents lack the toxic and carcinogenic properties found in HMPA.

Any of the variety of metal oxoanionic salts available may be employed in the present process. Preferable metal oxoanionic salts include Li$_2$B$_4$O$_7$, Li$_2$B$_{10}$O$_{16}$, Li$_2$SiO$_3$, Li$_3$PO$_4$, Li$_2$WO$_4$, Li$_2$CrO$_4$, Li$_2$MoO$_4$, LiTiO$_3$, LiCoO$_2$, Li$_2$CO$_3$, Li$_2$SO$_4$, Li$_2$SnO$_4$, Li$_3$VO$_4$, Li$_2$TeO$_4$, Na$_2$B$_4$O$_7$, Na$_2$B$_{10}$O$_{16}$, Na$_2$SiO$_3$, Na$_3$PO$_4$, Na$_2$WO$_4$, Na$_2$CrO$_4$, Na$_2$MoO$_4$, NaTiO$_3$, NaCoO$_2$, Na$_2$CO$_3$, Na$_2$SO$_4$, Na$_2$SnO$_4$, Na$_3$VO$_4$, Na$_2$TeO$_4$, K$_2$B$_4$O$_7$, K$_2$B$_{10}$O$_{16}$, K$_2$SiO$_3$, K$_3$PO$_4$, K$_2$WO$_4$, K$_2$CrO$_4$, K$_2$MoO$_4$, KTiO$_3$, KCoO$_2$, K$_2$CO$_3$, K$_2$SO$_2$, KL$_2$SnO$_4$, K$_3$VO$_4$, K$_2$TeO$_4$, MgB$_4$O$_7$, MgB$_{10}$O$_{16}$, MgSio$_3$, Mg$_3$(PO$_4$)$_2$, MgWO$_4$, MgCrO$_4$, MgMoO$_4$, Mg(TiO$_3$)$_2$, Mg(CoO$_2$)$_2$, MgCO$_3$, MgSO$_4$, CaB$_4$O$_7$, CaB$_{10}$O$_{16}$, CaSiO$_3$, Ca$_3$(PO$_4$)$_2$, CaWO$_4$, CaCrO$_4$, Ca(TiO$_3$)$_2$, Ca(CoO$_2$)$_2$, CaCO$_3$, CaSO$_4$, Cu$_2$B$_4$O$_7$, Cu$_2$B$_{10}$O$_{16}$, Cu$_2$SiO$_3$, Cu$_3$PO$_4$, Cu$_2$WO$_4$, Cu$_2$CrO$_4$, Cu$_2$MoO$_4$, CuTiO$_3$, CuCoO$_2$, Cu$_2$CO$_3$, Cu$_2$SO$_4$, CuB$_4$O$_7$, CuB$_{10}$O$_{16}$, CuSiO$_3$, Cu$_3$(PO$_4$)$_2$, CuWO$_4$, CuCrO$_4$, CuMoO$_4$, Cu(TiO$_3$)$_2$, Cu(CoO$_2$)$_2$, CuCO$_3$, CuSO$_4$, Ag$_2$B$_4$O$_7$, Ag$_2$B$_{10}$O$_{16}$, Ag$_2$SiO$_3$, Ag$_3$PO$_4$, Ag$_2$WO$_4$, Ag$_2$CrO$_4$, AgTiO$_3$, AgCoO$_2$, Ag$_2$CO$_3$, Ag$_2$SO$_4$, Al$_2$(B$_4$O$_7$)$_3$, Alphd 2(B$_{10}$O$_{16}$)$_3$, Al$_2$(SiO$_3$)$_3$, AlPO$_4$, Al$_2$(WO$_4$)$_3$, Al$_2$(CrO$_4$)$_3$, Al$_2$(MoO$_4$)$_3$, Al(TiO$_3$)$_3$, Al(CoO$_2$)$_3$, Al$_2$(CO$_3$)$_3$, Al$_2$(SO$_4$)$_3$, SnB$_4$B$_7$, SnB$_{10}$O$_{16}$, SnSiO$_3$, Sn$_3$(PO$_4$)$_2$, SnWO$_4$, SnCr O$_4$, SnMoO$_4$, Sn(TiO$_3$)$_2$, Sn(COO$_2$)$_2$, SnSO$_3$, SNSO$_4$, SN(B$_4$O$_7$)$_2$, Sn(B$_{10}$O$_{16}$)$_2$, Sn(SiO$_3$)$_2$, Sn$_3$(PO$_4$)$_4$, Sn(WO$_4$)$_2$, Sn(CrO$_4$)$_2$, Sn(MoO$_4$)$_2$, Sn(TiO$_3$)$_4$, Sn(CoO$_2$)$_4$, Sn(CO$_3$)$_2$, Sn(SO$_4$)$_2$, PdB$_4$O$_7$, Pd(B$_{10}$O$_{16}$, PdSio$_3$, Pd$_3$Pd$_3$(PO$_4$)$_2$, PdWO$_4$, PdCrO$_4$, PdMoO$_4$, Pd(TiO$_3$)$_2$, Pd(CoO$_2$)$_2$, PdCO$_3$, PdSO$_4$, Pd(B$_4$O$_7$)$_2$, Pd(B$_{10}$O$_{16}$)$_2$, Pd(SiO$_3$)$_2$, Pd$_3$(PO$_4$)$_4$, Pd(WO$_4$)$_2$, Pd(CrO$_4$)$_2$, Pd(MoO$_4$)$_2$, Pd(TiO$_3$)$_4$, Pd(CoO$_2$)$_4$, Pd(CO$_3$)$_2$, and Pd(SO$_4$)$_2$.

More preferably, the metal oxoanionic salt is selected from the group consisting of Li$_2$B$_4$O$_7$, Li$_2$B$_{10}$O$_{16}$, Li$_2$SiO$_3$, Li$_2$MoO$_4$, Na$_2$B$_4$O$_7$, Na$_2$B$_{10}$O$_{16}$, Na$_2$SiO$_3$, Na$_2$Mo O$_4$, K$_2$B$_4$O$_7$, K$_2$B$_{10}$O$_{16}$, K$_2$SiO$_3$, K$_2$MoO$_4$, MgB$_4$O$_7$, MgB$_{10}$O$_{16}$, MgSiO$_3$, MgMoO$_4$, Cu$_2$B$_4$O$_7$, Cu$_2$B$_{10}$O$_{16}$, Cu$_2$SiO$_3$, Cu$_2$MoO$_4$, CuB$_4$O$_7$, CuB$_{10}$O$_{16}$, CuSiO$_3$, CuMoO$_4$, SnB$_4$O$_7$, SnB$_{10}$O$_{16}$, SnSiO$_3$, SnMoO$_4$, Sn(B$_4$O$_7$)$_2$, Sn(B$_{10}$O$_{16}$)$_2$, Sn(SiO$_3$)$_2$ and Sn(MoO$_4$)$_2$. Most preferably, the metal oxoanionic salt is selected from the group consisting of Li$_2$MoO$_4$, Na$_2$MoO$_4$ and K$_2$MoO$_4$.

As one skilled in the art will recognize, such salts may, if desired, be formed in situ.

Suitable phase transfer agents include onium salts such as ammonium, phosphonium and sulfonium salts. Other phase transfer agents suitable for use in the present process will be readily apparent to those skilled in the art, armed with the present disclosure.

Various quaternary ammonium salt phase transfer agents are suitable for use in the present invention, as will be readily apparent to those skilled in the art. Preferably, the quaternary ammonium salt phase transfer agents consist of a nitrogen compound having three C$_1$–C$_3$ alkyl substitutes and one C$_{10}$–C$_{20}$ alkyl substituent on the nitrogen species or, alternatively, the nitrogen is incorporated in an aromatic ring structure, like a pyridine or quinoline structure, with a fourth nitrogen valence being supplied by a C$_{10}$–C$_{20}$ alkyl substituent. Preferably, the salt is a halide salt. Most preferably, the agents are selected from the group consisting of cetyltrimethylammonium chloride ("CTAC"), cetyltrimethyl-ammonium bromide ("CTAB"), dodecyltrimethylammonium chloride ("DTAC"), dodecyltrimethylammonium bromide ("DTAB"), cetylpyridinium chloride ("CPC"), and cetyl-pyridinium bromide ("CPB").

Various quaternary phosphonium salt phase transfer agents are also suitable for use in the present invention, as will be readily apparent to those skilled in the art. Preferably, the salt is a halide salt. Most preferably, the agents are quaternary phosphonium halides selected from the group consisting of tributyldecyl-phosphonium iodide, triphenyldecylphosphonium iodide, tributylhexadecylphosphonium iodide, hexadecyltributyl-phosphonium bromide, and homologues thereof having chlorine, fluorine, bromine or iodine atoms substituted for the specified halogen atom. As one skilled in the art would recognize, trisubstituted phosphine compounds substituted with hydrocarbons, such as tri-n-butyl phosphine, may be converted to quaternary phosphonium salts under the present reaction conditions, and as such, are also suitable for use in the subject process as phase transfer agents.

Representative sulfonium salt phase transfer agents include ternary sulfonium halides such as lauryl-dimethylsulfonium iodide, and homologues thereof having chlorine, fluorine or bromine atoms substituted for the iodine atom. As one skilled in the art would recognize, disubstituted sulfur compounds substituted with hydrocarbons may be converted to ternary sulfonium salts under the present reaction conditions, and as such, are also suitable for use in the subject process as phase transfer agents.

The amount of myrcene, palladium (II) chloride, metal oxoanionic salt, phase transfer agent, water and immiscible solvent employed in the foregoing process can vary widely, as will be recognized by those skilled in the art. By way of guidance, however, palladium (II) chloride and phase transfer agent are preferably present in about equal amounts, and preferably each are present in a molar amount equal to about 0.1 to about 0.6 times the molar amount of myrcene employed. Metal oxoanionic salt is preferably present in a molar amount equal to about 4 to about 10 times the molar amount of the palladium (II) chloride utilized. The water and immiscible solvent preferably together comprise about 70% to about 90% of the total reaction mixture volume, the water and immiscible solvent combination being comprised of about 25% to about 75% of immiscible solvent and a corresponding amount of about 25% to about 75% of water, on a total water and immiscible solvent volume basis.

The foregoing reaction proceeds best at temperatures ranging from about 80° C. to at least about 90° C., although higher or lower temperatures may be employed, if desired. The reaction may be conducted at atmospheric pressure, and generally runs to completion within a few hours. To maximize yields, slow but continual stirring, such as by use of a magnetic stirrer, may be employed. If desired, the reaction may be carried out in an inert atmosphere, such as in the presence of, for example, nitrogen, carbon dioxide, or argon gas.

In a preferable embodiment, the foregoing process is carried out in the presence of an oxidizing agent. Such oxidizing agents include, for example, hydrogen peroxide, benzoquinone, copper (II) salts such as copper chloride, cerium (IV) salts, iron (III) salts and silver (I) salts. Other suitable oxidizing agents will be apparent to those skilled in the art. As a skilled artisan would recognize, where copper (II) or iron (III) salts are employed, for example, oxygen or air may, if desired, be introduced into the reaction vessel to assist in reoxidation of the metal salts. Preferably, the oxidizing agent is selected from the group consisting of hydrogen peroxide, benzoquinone and copper (II) salts, particularly copper chloride. Most preferably, the oxidizing agent is hydrogen peroxide or copper (II) salts, particularly copper chloride.

The amount of oxidizing agent employed can vary widely as will be readily apparent to those skilled in the art. Preferably, the oxidizing agent is added in a molar amount equal to about 1 to about 5 times the molar amount of the palladium (II) chloride utilized.

The present invention further contemplates a process for producing citral comprising contacting a palladium-myrcene complex of the formula

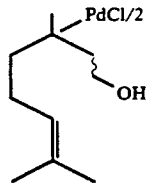

with a phase transfer agent, and a metal oxoanionic salt, in the presence of water and an immiscible solvent.

The palladium-myrcene complex employed can be obtained by using a number of different methods known to those skilled in the art, such as the methods disclosed in Takahashi et.al., *Journal of Organometallic Chemistry*, Vol. 266, pp. 327–336 (1984). The palladium-myrcene complex can also be produced using the processes described in copending application U.S. Serial No. 269,278, filed on Nov. 9, 1988, and entitled "Processes for the Conversion of Myrcene to Nerol and Citral", and copending application U.S. Ser. No. 363,808, filed on June 9, 1989, and entitled "Processes for the Conversion of Myrcene to Citral", the disclosures of each of which are hereby incorporated by reference herein.

The immiscible solvents, metal oxoanionic salts, and phase transfer agents which may be employed in the latter embodiment of the invention, including the preferences therefor, are as previously described.

The amount of palladium-myrcene complex, metal oxoanionic salt, phase transfer agent, water and immiscible solvent employed in the latter process can vary widely, as will be recognized by those skilled in the art. By way of guidance, however, the metal oxoanionic salt is preferably employed in a molar amount equal to about 5 to about 20 times the molar amount of palladium-myrcene complex employed. The water and immiscible solvent preferably together comprise about 70% to about 90% of the total reaction mixture volume, the water and immiscible solvent combination being comprised of about 25% to about 75% of immiscible solvent, and a corresponding amount of about 25% to about 75% of water, on a total water and immiscible solvent volume basis.

Preferably, the latter reaction is carried out at temperatures ranging from about 80° C. to about 90° C., although as will be understood by those skilled in the art, higher or lower temperatures may be employed.

The foregoing processes clearly provide efficient and commercially viable pathways to the important compound citral.

The citral compound produced by the subject processes is useful in a variety of ways, for example, it may be employed as a fragrance or a flavor additive or as a precursor for the synthesis of vitamins A and E. See Derfer et.al., "Terpenoids", pp. 709–762 in *Kirk-Othmer Encyclopedia of Chemical Technology*, 3rd ed., Vol. 22, Wiley Interscience Publications (New York, 1983), the disclosures of which are incorporated by reference herein.

The present invention is further described in the following Examples. These Examples are not to be construed as limiting the scope of the appended Claims.

EXAMPLES

In the Examples which follow, the myrcene employed was a myrcene and limonene mixture in a ratio of about 80 to about 20, respectively, obtained from Aldrich Chemical Company, Milwaukee, Wisconsin. The cetyltrimethylammonium chloride was used as an aqueous solution, 25% by weight, also obtained from Aldrich.

The resulting products were analyzed using internal standard gas chromatography (GC), unless otherwise noted, and yield results recorded. Yield calculations in all of the Examples are based on the initial level of the palladium (II) salt.

EXAMPLE 1

A solution of $CuCl_2$ (0.1528 g), $PdCl_2(CH_3CN)_2$ (0.3008 g), $Li_2MoO_4$ (1.1047 g) and $H_2O$ (3.5 ml) was prepared. The solution was stirred at room temperature for about 10 min. To the solution was then added myrcene (0.66 ml), toluene (7.5 ml) and cetyltrimethylammonium chloride (1.5 ml). Carbon dioxide was bubbled through for about 20 min, the solution was heated to about 90° C. for about 2.5 hrs, and product recovered.

The resulting yield of citral was 27%.

EXAMPLE 2

A solution of $CuCl_2$ (0.15-12 g), $PdCl_2(CH_3CN)_2$ (0.3008 g), $Li_2MoO_4$ (1.1031 g) and $H_2O$ (5 ml) was prepared. The solution was stirred at room temperature for about 10 min. To the solution was then added myrcene (0.66 ml), toluene (7.5 ml) and cetyltrimethylammonium bromide (0.4157 g). Carbon dioxide was bubbled through for about 20 min, the solution was heated to about 90° C. for about 2.5 hrs, and product recovered.

The resulting yield of citral was 14%.

EXAMPLE 3

A solution of $CuCl_2$ (0.1520 g), $PdCl_2(CH_3CN)_2$ (0.3000 g), $Li_2MoO_4$ (1.1046 g) and $H_2O$ (3.67 ml) was prepared. The solution was stirred at room temperature for about 10 min. To the solution was then added myrcene (0.66 ml), n-butanol (7.5 ml) and cetyltrimethylammonium chloride (1.32 ml). Carbon dioxide was bubbled through for about 20 min, the solution was heated to about 90° C. for about 2.5 hrs, and product recovered.

The resulting yield of citral was 46%.

EXAMPLE 4

A solution of $CuCl_2$ (0.0675 g), $PdCl_2(CH_3CN)_2$ (0.1300 g), $Li_2MoO_4$ (0.4849 g) and $H_2O$ (3.67 ml) was prepared. The solution was stirred at room temperature for about 10 min. To the solution was then added myrcene (3 ml), n-butanol (7.5 ml) and cetyltrimethylammonium chloride (1.32 ml), and $O_2$ was bubbled through the solution for about 15 min. The solution was heated to about 90° C. for about 6 hrs, while continuing to introduce $O_2$ into the reaction vessel. Product was then recovered.

The resulting yield of citral was 43%.

EXAMPLE 5

A solution of $CuCl_2$ (0.0678 g), $PdCl_2(CH_3CN)_2$ (0.1308 g), $Li_2MoO_4$ (0.4764 g) and $H_2O$ (3.67 ml) was prepared. The solution was stirred at room temperature for about 10 min. To the solution was then added myrcene (3 ml), n-butanol (7.5 ml) and cetyltrimethylammonium chloride (1.32 ml), and $O_2$ was bubbled through the solution for about 15 min. The solution was heated to about 90° C. for overnight, while continuing to introduce $O_2$ into the reaction vessel. Product was then recovered.

The resulting yield of citral was 66%.

EXAMPLE 6

A solution of $CuCl_2$ (0.0678 g), $PdCl_2(CH_3CN)_2$ (0.1312 g), $Li_2MoO_4$ (0.4782 g) and $H_2O$ (5 ml) was prepared. The solution was stirred at room temperature for about 10 min. To the solution was then added myrcene (3 ml), n-butanol (7.5 ml) and cetylpyridinium chloride (0.3586 g). Carbon dioxide was bubbled through for about 20 min, the solution was heated to about 90° C. for about 2.5 hrs, and product recovered.

The resulting yield of citral was 66%.

EXAMPLE 7

A solution of $CuCl_2$ (0.6731 g), $PdCl_2(CH_3CN)_2$ (0.0886 g), $Li_2MoO_4$ (1.0042 g) and $H_2O$ (5 ml) was prepared. The solution was stirred at room temperature for about 10 min. To the solution was then added myrcene (2.83 ml), toluene (7.5 ml) and cetyltrimethylammonium chloride (1.32 ml). Oxygen was bubbled through for about 20 min, the solution was heated to about 90° C. for about 4 hrs, and product recovered.

The resulting yield of citral, analyzed using external standard gas chromatography, was 20%.

EXAMPLE 8

A solution of $CuCl_2$ (0.1522 g), $PdCl_2(CH_3CN)_2$ (0.3010 g), $Li_2MoO_4$ (1.1047 g) and $H_2O$ (5 ml) was prepared. The solution was stirred at room temperature for about 10 min. To the solution then added myrcene (0.66 ml), 1-butanol (7.5 ml) and hexadecyltributylphosphonium bromide (0.5077 g), and $CO_2$ was bubbled through the solution for about 15 min. The solution was heated to about 90° C. for about 2.5 hours, while continuing to introduce $CO_2$ into the reaction vessel. Product was then recovered.

The resulting yield of citral was 12%.

Various modifications of the invention in addition to those shown and described herein will be apparent to those skilled in the art from the foregoing description. Such modifications are also intended to fall within the scope of the appended claims.

What is claimed is:

1. A process for producing citral comprising contacting myrcene with palladium (II) chloride in the presence of water, a solvent immiscible with water, a phase transfer agent, and a metal oxoanionic salt wherein said metal of said metal oxoanionic salt is selected from the group consisting of Li, Na, K, Mg, Ca, Cu, Ag, Al, Sn, and Pd.

2. A process according to claim 1 wherein the process is carried out at a temperature ranging from about 80° C. to about 90° C.

3. A process according to claim 1 wherein the palladium (II) chloride is selected from the group consisting of $PdCl_2$ and $PdCl_2$ loosely coordinated with ligand donors.

4. A porcess according to claim 3 wherein the palladium (II) chloride is dichlorobisacetonitrile palladium.

5. A process according to claim 1 wherein the immiscible solvent is selected from the group consisting of substituted and unsubstituted aromatic compounds and substituted $C_3$ to $C_{12}$ alkyls wherein the alkyl is substituted with one or more hydroxy, ketone, ether or cyano groups.

6. A process according to claim 5 wherein the solvent is selected from the group consisting of substituted aromatic compounds and substituted $C_3$ to $C_{12}$ alkyls wherein the alkyl is substituted with one or more hydroxy groups.

7. A process according to claim 6 wherein the solvent is selected from the group consisting of toluene and 1-butanol.

8. A process according to claim 1 wherein the metal oxoanionic salt is selected from the group consisting of $Li_2B_4O_7$, $Li_2B_{10}O_{16}$, $Li_3PO_4$, $Li_2WO_4$, $Li_2CrO_4$, $Li_2MoO_4$, $LiTiO_3$, $LiCoO_2$, $Li_2CO_3$, $Li_2SO_4$, $Na_2B_4O_7$, $Na_2B_{10}O_{16}$, $Na_2SiO_3$, $Na_3PO_4$, $Na_2WO_4$, $Na_2CrO_4$, $Na_2MoO_4$, $NaTiO_3$, $NaCoO_2$, $Na_2CO_3$, $Na_2SO_4$, $K_2B_4O_7$, $K_2B_{10}O_{16}$, $K_2SiO_3$, $K_3PO_4$, $KL_2WO_4$, $K_2CrO_4$, $K_2MoO_4$, $KTiO_3$, $KLCoO_2$, $K_2CO_3$, $K_2SO_4$, $MgB_4O_7$, $MgB_{10}O_{16}$, $MgSiO_3$, $Mg_3(PO_4)_2$, $MgWO_4$, $MgCrO_4$, $MgMoO_4$, $Mg(TiO_3)_2$, $Mg(CoO_2)_2$, $MgCO_3$, $MgSO_4$, $CaB_4O_7$, $CaB_{10}O_{16}$, $CaSiO_3$, $Ca_3(PO_4)_2$, CaWO$_4$, CaCrO$_4$, Ca(TiO$_3$)$_2$, Ca(CoO$_2$)$_2$, CaCO$_3$, CaSO$_4$, Cu$_2$B$_4$O$_7$, Cu$_2$B$_{10}$O$_{16}$, Cu$_2$SiO$_3$, CU$_3$PO$_4$, Cu$_2$WO$_4$, Cu$_2$CrO$_4$, Cu$_2$MoO$_4$, CuTiO$_3$, CuCoO$_2$, Cu$_2$Co$_3$, Cu$_2$SO$_4$, CuB$_4$B$_4$O$_7$, CuB$_{10}$O$_{16}$, CuSiO$_3$, Cu$_3$(PO$_4$)$_2$, CuWO$_4$, CuCrO$_4$, CuMoO$_4$, Cu(TiO$_3$)$_2$, Cu(CoO$_2$)$_2$, CuCO$_3$, CuSO$_4$, Ag$_2$B$_4$O$_7$, Ag$_2$B$_{10}$O$_{16}$, Ag$_2$SiO$_3$, Ag$_3$PO$_4$, Ag$_2$WO$_4$, Ag$_2$CrO$_4$, AgTiO$_3$, AgCoO$_2$, Ag$_2$CO$_3$, Ag$_2$SO$_4$, Al$_2$(B$_4$O$_7$)$_3$, Al$_2$($_{10}$O$_{16}$)$_3$, Al$_2$(SiO$_3$)$_3$, AlPO$_4$, Al$_2$(WO$_4$)$_3$, Al$_2$(CrO$_4$)$_3$, Al$_2$(MoO$_4$)$_3$, Al(TiO$_3$)$_3$, Al(CoO$_2$)$_3$, Al$_2$(CO$_3$)$_3$, Al$_2$(SO$_4$)$_3$, SnB$_4$O$_7$, SnB$_{10}$O$_{16}$, SnSiO$_3$, Sn$_3$(PO$_4$)$_2$, SnWO$_4$, SnCrO$_4$, SnMoO$_4$, Sn(TiO$_3$)$_2$, Sn(CoO$_2$)$_2$, SnCO$_3$, SnSO$_4$, Sn(B$_4$O$_7$)$_2$, Sn(B$_{10}$O$_{16}$)$_2$, Sn(SiO$_3$)$_2$, Sn$_3$(PO$_4$)$_4$, Sn(WO$_4$)$_2$, Sn(CrO$_4$)$_2$, Sn(MoO$_4$)$_2$, Sn(TiO$_3$)$_4$, Sn(CoO$_2$)$_4$, Sn(CO$_3$)$_2$, Sn(SO$_4$)$_2$, PdB$_4$O$_7$, PdB$_{10}$O$_{16}$, PdSiO$_3$, Pd$_3$(PO$_4$)$_2$, PdWO$_4$, PdCrO$_4$, PdMoO$_4$, Pd(TiO$_3$)$_2$, Pd(CoO$_2$)$_2$, PdCO$_3$, OdCO$_3$, PdSO$_4$, Pd(B$_4$O$_7$)$_2$, Pd(B$_{10}$O$_{16}$)$_2$, Pd(SiO$_3$)$_2$, Pd$_3$(PO$_4$, Pd(WO$_4$)$_2$, Pd(CrO$_4$)$_2$, Pd(MoO$_4$)$_2$, Pd(TiO$_3$)$_4$, Pd(CoO$_2$)$_4$, Pd(CO$_3$)$_2$, and Pd(SO$_4$)$_2$.

9. A process according to claim 8 wherein the metal oxide is selected from the group consisting of Li$_2$MoO$_4$ and K$_2$MoO$_4$.

10. A process according to claim 1 wherein the myrcene is in the form of a myrcene and limonene mixture.

11. A process according to claim 10 wherein the myrcene to limonene ratio is about 80 to about 20.

12. A process according to claim 1 which is carried out in the presence of an oxidizing agent.

13. A process according to claim 1 wherein the phase transfer agent is selected from the group consisting of ammonium, phosphonium and sulfonium salts.

14. A process according to claim 13 wherein the phase transfer agent is a quaternary ammonium salt.

15. A process according to claim 14 wherein the quaternary ammonium salt is selected from the group consisting of cetyltrimethylammonium chloride, cetyltrimethylammonium bromide, dodecyltrimethylammonium chloride, dodecyltrimethylammonium bromide, cetylpyridinium chloride, and cetylpyridinium bromide.

16. A process for producing citral comprising contacting a palladium-myrcene complex of the formula

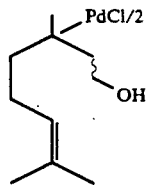

with a phase transfer agent, and a metal oxoanionic salt wherein said metal of said metal oxoanionic salt is selected from the group consisting of Li, Na, K, Mg, Ca, Cu, Ag, Al, Sn, and Pd, in the presence of water and a solvent immiscible with water.

17. A process according to claim 16 wherein the process is carried out at a temperature ranging from about 80° C. to about 90° C.

18. A process according to claim 16 wherein the solvent is selected from the group consisting of substituted and unsubstituted aromatic compounds and substituted C$_3$ to C$_{12}$ alkyls wherein the alkyl is substituted with one or more hydroxy, ketone, ether or cyano groups.

19. A process according to claim 18 wherein the solvent is selected from the group consisting of substituted aromatic compounds and substituted C$_3$ to C$_{12}$ alkyls wherein the alkyl is substituted with one or more hydroxy groups.

20. A process according to claim 19 wherein the solvent is selected from the group consisting of toluene and 1-butanol.

21. A process according to claim 16 wherein the metal oxoanionic salt is selected from the group consisting of Li$_2$B$_4$O$_7$, Li$_2$B$_{10}$O$_{16}$, Li$_2$SiO$_3$, Li$_3$PO$_4$, Li$_2$WO$_4$, Li$_2$CrO$_4$, Li$_2$MoO$_4$, LiTiO$_3$, LiCoO$_2$, Li$_2$CO$_3$, Li$_2$SO$_4$, Na$_2$B$_4$O$_7$, Na$_2$B$_1$o$_{16}$, Na$_2$SiO$_3$, Na$_3$PO$_4$, Na$_2$WO$_4$, Na$_2$CrO$_4$, Na$_2$MoO$_4$, NaTiO$_3$, NaCoO$_2$, Na$_2$CO$_3$, Na$_2$SO$_4$, K$_2$B$_4$O$_7$, K$_2$B$_{10}$O$_{16}$, K$_2$SiO$_3$, K$_3$PO$_4$, K$_2$WO$_4$, K$_2$CrO$_4$, K$_2$MoO$_4$, KTiO$_3$, KCoO$_2$, K$_2$CO$_3$, K$_2$SO$_4$, MgB$_4$O$_7$, MgB$_{10}$O$_{16}$, MgSiO$_3$, Mg$_3$(PO$_4$)$_2$, MgWO$_4$, MgCrO$_4$, MgMoO$_4$, Mg(TiO$_3$)$_2$, Mg(CoO$_2$)$_2$, MgCO$_3$, MgSO$_4$, CaB$_4$O$_7$, CaB$_{10}$O$_{16}$, CaSiO$_3$, Ca$_3$(PO$_4$)$_2$, CaWO$_4$, CaCrO$_4$, Ca(TiO$_3$)$_2$, Ca(CoO$_2$)$_2$, CaCO$_3$, CaSO$_4$, Cu$_2$B$_4$O$_7$, Cu$_2$B$_{10}$O$_{16}$, Cu$_2$SiO$_2$, Cu$_3$PO$_4$, Cu$_2$WO$_4$, Cu$_2$CrO$_4$, Cu$_2$MoO$_4$, CuTiO$_3$, CuCoO$_2$, Cu$_2$CO$_3$, Cu$_2$SO$_4$, CuB$_4$O$_7$, CuB$_{10}$O$_{16}$, CuSiO$_3$, Cu$_3$(PO$_4$)$_2$, CuWO$_4$, CuCrO$_4$, CuMoO$_4$, Cu(TiO$_3$)$_2$, Cu(CoO$_2$)$_2$, CuCO$_3$, CuSO$_4$, Ag$_2$B$_4$O$_7$, Ag$_2$B$_{10}$O$_{16}$, Ag$_2$SiO$_3$, Ag$_3$PO$_4$, Ag$_2$WO$_4$, Ag$_2$CrO$_4$, AgTiO$_3$, AgCoO$_2$, Ag$_2$CO$_3$, Ag$_2$SO$_4$, Al$_2$(B$_4$O$_7$)$_3$, Al$_2$(B$_{10}$O$_{16}$)$_3$, Al$_2$(SiO$_3$)$_3$, AlPO$_4$, Al$_2$(WO$_4$)$_3$, Al$_2$(CrO$_4$)$_3$, Al$_2$(MoO$_4$)$_3$, Al(TiO$_3$)$_3$, Al(CoO$_2$)$_3$, Al$_2$(CO$_3$)$_3$, Al$_2$(SO$_4$)$_3$, SnB$_4$O$_7$, SnB$_{10}$O$_{16}$, SnSiO$_3$, Sn$_3$(PO$_4$)$_2$, SnWO$_4$, SnCrO$_4$, SnMoO$_4$, Sn(TiO$_3$)$_2$, Sn(CoO$_2$)$_2$, SnCO$_3$, SnSO$_4$, Sn(B$_4$O$_7$)$_2$, Sn(B$_{10}$O$_{16}$)$_2$, Sn(SiO$_3$)$_2$, Sn$_3$(PO$_3$)$_4$, Sn(WO$_4$)$_2$, Sn(CrO$_4$)$_2$, Sn(MoO$_4$)$_2$, Sn(TiO$_3$)$_4$, Sn(CoO$_2$)$_4$, Sn(CO$_3$)$_2$, Sn(SO$_4$)$_2$, PdB$_4$O$_7$, PdB$_{10}$O$_{16}$, PdSiO$_3$, Pd$_3$(PO$_4$)$_2$, PdWO$_4$, PdCrO$_4$, PdMoO$_4$, Pd(TiO$_3$)$_2$, Pd(CoO$_2$)$_2$, PdCO$_3$, PdSO$_4$, Pd(B$_4$O$_7$)$_2$, Pd(B$_{10}$O$_{16}$)$_2$, Pd(SiO$_3$)$_2$, Pd$_3$(PO$_4$)$_4$, Pd(WO$_4$)$_2$, Pd(*CrO$_4$)$_2$, Pd(MoO$_4$)$_2$, Pd(TiO$_3$)$_4$, Pd(CoO$_2$)$_4$, Pd(CO$_3$)$_2$, and Pd(SO$_4$)$_2$.

22. A process according to Claim 21 wherein the metal oxoanionic, salt is selected from the group consisting Li$_2$MoO$_4$, Na$_2$MoO$_4$ and K$_2$MoO$_4$.

23. A process according to claim 16 wherein the phase transfer agent is selected from the group consisting of ammonium, phosphonium and sulfonium salts.

24. A process according to claim 23 wherein the phase transfer agent is a quaternary ammonium salt.

25. A process according to claim 24 wherein the quaternary ammonium salt is selected from the group consisting of cetyltrimethylammonium chloride, cetyltri-methylammonium bromide, dodecyltrimethylammonium chloride, dodecyltrimethylammonium bromide, cetyl-pyridinium chloride, and cetylpyridinium bromide.

* * * * *